(12) United States Patent
Watanabe

(10) Patent No.: US 8,492,596 B2
(45) Date of Patent: Jul. 23, 2013

(54) PROCESS FOR PRODUCTION OF DITRIMETHYLOLPROPANE

(75) Inventor: Masafumi Watanabe, Kurashiki (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 485 days.

(21) Appl. No.: 12/739,019

(22) PCT Filed: Oct. 17, 2008

(86) PCT No.: PCT/JP2008/068863
§ 371 (c)(1),
(2), (4) Date: Apr. 21, 2010

(87) PCT Pub. No.: WO2009/057466
PCT Pub. Date: May 7, 2009

(65) Prior Publication Data
US 2010/0240931 A1  Sep. 23, 2010

(30) Foreign Application Priority Data

Oct. 30, 2007 (JP) ................. 2007-281509
Dec. 14, 2007 (JP) ................. 2007-323792

(51) Int. Cl.
*C07C 41/01* (2006.01)
(52) U.S. Cl.
USPC ....................................... 568/680
(58) Field of Classification Search
USPC ....................................... 568/680
See application file for complete search history.

(56) References Cited

U.S. PATENT DOCUMENTS

| | | | |
|---|---|---|---|
| 3,097,245 A * | 7/1963 | Russell et al. ............. | 568/853 |
| 3,962,347 A | 6/1976 | Herz | |
| 5,324,863 A | 6/1994 | Sjogreen et al. | |
| 5,840,994 A | 11/1998 | Ninomiya et al. | |
| 6,080,896 A | 6/2000 | Ninomiya et al. | |

FOREIGN PATENT DOCUMENTS

| | | |
|---|---|---|
| EP | 0 799 815 A1 | 10/1997 |
| JP | 47 30611 | 11/1972 |
| JP | 57 011934 | 1/1982 |
| JP | 57 139028 | 8/1982 |
| JP | 57 142929 | 9/1982 |
| JP | 8 157401 | 6/1996 |
| JP | 9 268150 | 10/1997 |
| JP | 2002 47231 | 2/2002 |
| JP | 2003 267904 | 9/2003 |
| JP | 2005 23067 | 1/2005 |

OTHER PUBLICATIONS

Extended Search Report issued May 31, 2012 in European Application No. 08844216.5.

* cited by examiner

*Primary Examiner* — Rosalynd Keys
(74) *Attorney, Agent, or Firm* — Oblon, Spivak, McClelland, Maier & Neustadt, L.L.P.

(57) ABSTRACT

The present invention provides a method for producing ditrimethylolpropane including reacting n-butyraldehyde with formaldehyde in the presence of a base catalyst to thereby produce trimethylolpropane and ditrimethylolpropane, wherein the method includes (I) a step of reacting n-butyraldehyde with formaldehyde (1) in the presence of a base catalyst (1), to thereby produce a reaction mixture containing trimethylolpropane, ditrimethylolpropane, and 2-ethyl-2-propenal; (II) a step of recovering 2-ethyl-2-propenal through distillation of the produced reaction mixture; and (III) a step of adding, to a distillation residue obtained through recovery of 2-ethyl-2-propenal, the recovered 2-ethyl-2-propenal and formaldehyde (2), and optionally a base catalyst (2), to thereby allow reaction for production of ditrimethylolpropane to proceed, wherein the amounts of formaldehyde (I) and the base catalyst (1) supplied in step I and formaldehyde (2) and the base catalyst (2) supplied in step II are controlled to specific amounts, to thereby effectively produce ditrimethylolpropane. According to the present invention, the yield of di-TMP is considerably increased, and the amount of bis-TMP by-produced can be considerably reduced with respect to the amount of di-TMP (i.e., a product of interest) produced; that is, di-TMP can be effectively produced in an industrially advantageous manner.

12 Claims, No Drawings

PROCESS FOR PRODUCTION OF DITRIMETHYLOLPROPANE

TECHNICAL FIELD

The present invention relates to a method for effectively producing ditrimethylolpropane through reaction between n-butyraldehyde and formaldehyde in the presence of a base catalyst.

BACKGROUND ART

When trimethylolpropane (hereinafter may be referred to as "TMP") is industrially produced through aldol condensation and crossed Cannizzaro reaction between n-butyraldehyde (hereinafter may be referred to as "NBD") and formaldehyde in the presence of a base catalyst, ditrimethylolpropane (hereinafter may be referred to as "di-TMP") is produced as a by-product, and di-TMP is recovered from a high-boiling-point mixture (Patent Document 1).

In a method for recovering di-TMP from such a high-boiling-point mixture, a reaction mixture of NBD and formaldehyde is subjected to solvent extraction after concentration or without concentration, to thereby produce a TMP extract (crude TMP) containing substantially no sodium formate, and the crude TMP is purified through distillation under high vacuum, to thereby produce a distillation residue containing 1 to 20% TMP and 20 to 50% di-TMP.

Proposed methods for recovering di-TMP from such a crude TMP distillation residue include a method of crystallization of di-TMP from ethyl acetate (Patent Document 2); a method of crystallization of di-TMP from water (solvent) in the presence of sodium formate (Patent Document 3); a method of crystallization of di-TMP from 1,4-dioxane (solvent) (Patent Document 4); and a method of crystallization of di-TMP from acetone (solvent) (Patent Document 5).

Such a method for recovering di-TMP from a distillation residue of TMP (i.e., main target product) is current employed as a general procedure for producing di-TMP. In such a di-TMP production method, only di-TMP must be separated and recovered from the TMP distillation residue, which contains formaldehyde and NBD (i.e., raw materials for production of TMP), modified products generated during recovery (through distillation) of TMP, and by-products other than di-TMP (e.g., acetal formed between TMP and formaldehyde). However, a low di-TMP content of the distillation residue makes it difficult to recover di-TMP at an industrially satisfactory yield.

Particularly, the distillation residue obtained upon TMP production contains bistrimethylolpropane (hereinafter may be referred to as "bis-TMP"), which is a linear formal formed from two TMP molecules and formaldehyde, and bis-TMP and di-TMP are difficult to separate from each other. Therefore, effective production of di-TMP requires considerable reduction in amount of bis-TMP by-produced.

Attempts have been made to effectively produce di-TMP by increasing the amount of di-TMP by-produced upon TMP production, and there has been proposed a method in which reaction is carried out under certain specific conditions (Patent Documents 6 and 7), as well as a method in which a water-insoluble organic solvent is added to the reaction system (Patent Document 8).

In such proposed methods, di-TMP is produced at a yield of about 10 mol % on the basis of NBD. That is, the amount of di-TMP by-produced through such a method is only twice or thrice that of di-TMP by-produced through the aforementioned conventional TMP production methods in which no measures are taken to increase the amount of di-TMP by-produced. Thus, di-TMP is a by-product of TMP production, and the amount of di-TMP produced is necessarily limited by the amount of TMP produced. Therefore, the aforementioned TMP production methods cannot meet increased demand for di-TMP.

The method described in Patent Document 8 in which a water-insoluble organic solvent is added to the reaction system for extraction of di-TMP is industrially very disadvantageous in that, after extraction, both the aqueous layer and the organic layer contain di-TMP (i.e., a compound of interest), and thus the method requires a very intricate post treatment after reaction and also requires recovery (through distillation) of a used organic solvent.

Meanwhile, there have been disclosed di-TMP synthesis methods, including a method in which an ether bond is formed through dehydration-condensation of two TMP molecules (Patent Document 9), and a method for synthesizing di-TMP through reaction between 2-ethyl-2-propenal (hereinafter may be referred to as "ECR") and TMP (Patent Document 10). Unlike the aforementioned methods for recovering di-TMP from a TMP distillation residue, such a di-TMP synthesis methods can meet increased demand for di-TMP, since the amount of di-TMP produced through the synthesis methods is not limited by the amount of TMP produced.

However, in the method in which an ether bond is formed through dehydration-condensation of two TMP molecules, since di-TMP is produced through reaction between TMP molecules, each having a structure including three alcoholic hydroxyl groups which can participate in reaction, by-production of an ether condensate of three or more TMP molecules, which would otherwise occurs inevitably, cannot be prevented. For suppression of such by-production, the percent reaction of dehydration-condensation between TMP molecules must be reduced, but accordingly high cost is required for recovery of unreacted TMP through distillation, resulting in an industrial disadvantage.

In order to solve such a problem, Patent Document 9 describes a method which uses, as a raw material, TMP in which some of three alcoholic hydroxyl groups have been esterified with a lower fatty acid in advance. However, this method cannot essentially solve the aforementioned problem of by-production of an ether condensate of three or more TMP molecules, due to the inability to selectively esterify only two alcoholic hydroxyl groups of one TMP molecule with a lower fatty acid. In addition, the method described in Patent Document 9 produces TMP in which one or two alcoholic hydroxyl groups have been esterified, and thus requires a new process for regenerating di-TMP through hydrolysis of di-TMP having esterified alcoholic hydroxyl groups, resulting in increased production cost and an industrial disadvantage.

In the method disclosed in Patent Document 10, even when TMP is used in a large excess amount with respect to ECR, the yield of di-TMP is less than 70% on the basis of ECR. This method is economically disadvantageous in that the method requires recovery of di-TMP, as well as recovery of excessively used TMP through distillation.

Patent Document 1: U.S. Pat. No. 3,097,245, specification
Patent Document 2: Japanese Patent Application Laid-Open (kokai) No. S47-30611
Patent Document 3: Japanese Patent Application Laid-Open (kokai) No. S49-133311
Patent Document 4: Japanese Patent Application Laid-Open (kokai) No. 2002-47231
Patent Document 5: Japanese Patent Application Laid-Open (kokai) No. 2005-23067

Patent Document 6: Japanese Patent Application Laid-Open (kokai) No. S57-139028
Patent Document 7: Japanese Patent Application Laid-Open (kokai) No. S57-142929
Patent Document 8: Japanese Patent Application Laid-Open (kokai) No. H08-157401
Patent Document 9: Japanese Kohyo Patent Publication No. H06-501470
Patent Document 10: Japanese Patent Application Laid-Open (kokai) No. H09-268150

DISCLOSURE OF THE INVENTION

Problems to be Solved by the Invention

With regard to the aforementioned conventional di-TMP production methods, methods (A) in which di-TMP is recovered from a distillation residue of TMP produced through reaction between n-butyraldehyde and formaldehyde in the presence of a base catalyst pose, for example, the following problems: (1) since the di-TMP content of the distillation residue is low, and di-TMP is a by-product of TMP production, the amount of di-TMP produced is necessarily limited by the amount of TMP produced, which cannot meet increased demand for di-TMP; and (2) di-TMP and bis-TMP are difficult to separate from each other. Meanwhile, methods (B) for synthesizing di-TMP pose problems in that, for example, the yield of di-TMP is low, and recovery of unreacted TMP through distillation requires high production cost.

An object of the present invention is to provide a method for effectively and industrially advantageously producing di-TMP through reaction between n-butyraldehyde and formaldehyde in the presence of a base catalyst.

Means for Solving the Problems

The present inventor has conducted extensive studies on di-TMP production methods which pose the aforementioned problems, and as a result has found that, in a method in which n-butyraldehyde is reacted with formaldehyde in the presence of a base catalyst, when by-produced ECR is separated through distillation, and the resultant distillation residue is reacted with ECR under specific conditions, di-TMP can be effectively produced. The present invention has been accomplished on the basis of this finding.

Accordingly, the present invention provides the following methods for producing di-TMP.

1. A method for producing ditrimethylolpropane comprising reacting n-butyraldehyde with formaldehyde in the presence of a base catalyst to thereby produce trimethylolpropane and ditrimethylolpropane, characterized in that the method comprises:

(I) a step of reacting n-butyraldehyde with formaldehyde (1) in the presence of a base catalyst (1), to thereby produce a reaction mixture containing trimethylolpropane, ditrimethylolpropane, and 2-ethyl-2-propenal;

(II) a step of recovering 2-ethyl-2-propenal through distillation of the reaction mixture produced in step I; and (III) a step of adding, to a distillation residue obtained through recovery of 2-ethyl-2-propenal in step II, the recovered 2-ethyl-2-propenal and formaldehyde (2), and optionally a base catalyst (2), to thereby allow reaction for production of ditrimethylolpropane to proceed, wherein, on the basis of 1.0 mol of n-butyraldehyde serving as a raw material, (a) the amount of formaldehyde (1) supplied is 2.0 to 3.5 mol; (b) the total amount of formaldehyde (1) and formaldehyde (2) supplied is 3.0 to 4.5 mol; (c) the amount of the base catalyst (1) supplied is 0.5 to 1.5 equivalents; (d) the total amount of the base catalyst (1) and the base catalyst (2) supplied is 1.0 to 2.5 equivalents; and (e) the amount of 2-ethyl-2-propenal recovered is 0.05 to 0.5 mol.

2. A method for producing ditrimethylolpropane according to 1 above, wherein the reaction temperature in step I is from 45 to 120° C.

3. A method for producing ditrimethylolpropane according to 1 or 2 above, wherein the distillation temperature in step II is from 45° C. to 120° C.

4. A method for producing ditrimethylolpropane according to any of 1 to 3 above, wherein, in step II, 2-ethyl-2-propenal is recovered in the form of a distillate mixture containing water in an amount of 0.01 to 20 times the mass of 2-ethyl-2-propenal distilled.

5. A method for producing ditrimethylolpropane according to any of 1 to 4 above, wherein, in step III, reaction is carried out at 45 to 120° C.

Effects of the Invention

According to the present invention, in a method for producing TMP through reaction between NBD and formaldehyde, ECR is recovered through distillation from the resultant reaction mixture, and the thus-recovered ECR is reacted with the distillation residue under specific conditions, whereby the yield of di-TMP is considerably increased. According to the present invention, the amount of bis-TMP by-produced can be considerably reduced with respect to the amount of di-TMP (i.e., a product of interest) produced; that is, di-TMP can be effectively produced. The method of the present invention is industrially very useful and advantageous, since, in the method, unreacted raw material (e.g., formaldehyde) having a boiling point lower than that of di-TMP can be recovered through distillation and recycled.

BEST MODES FOR CARRYING OUT THE INVENTION

Ditrimethylolpropane (di-TMP), which is a product of interest produced through the method of the present invention, is represented by the following chemical formula.

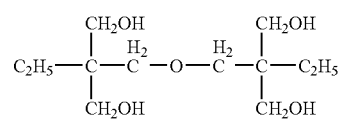
[F1]

Bistrimethylolpropane (bis-TMP), which is by-produced as a high-boiling-point substance, is represented by the following chemical formula.

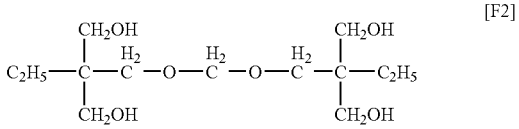 [SMILES: CCC(CO)(CO)COCOCC(CC)(CO)CO]
[F2]

The method for producing di-TMP of the present invention includes the following three steps: step I of reacting NBD with formaldehyde (1) in the presence of a base catalyst (1); step II of recovering ECR through distillation from the resultant reaction mixture; and step III of adding, to the resultant distillation residue, ECR and formaldehyde (2), and optionally a base catalyst (2), to thereby allow reaction for production of di-TMP to proceed.

The method for producing di-TMP of the present invention may employ, as a raw material, generally commercially available NBD as is. Alternatively, commercially available NBD employed in the present invention may optionally be further purified through, for example, distillation.

Formaldehyde (i.e., another raw material) employed in the method of the present invention may be in the form of aqueous formaldehyde solution or solid paraformaldehyde. Aqueous formaldehyde solution generally contains methanol serving as a stabilizer in an amount of several mass %. The method may optionally employ an aqueous formaldehyde solution from which methanol has been separated through, for example, distillation. In the method, formaldehyde is supplied in step I and step III. As used herein, "formaldehyde (1)" refers to one supplied in step I, and "formaldehyde (2)" refers to one supplied in step III.

The base catalyst employed in the present invention may be an inorganic base or an organic base. Examples of the inorganic base include hydroxides and carbonates of alkali metals and alkaline earth metals, such as sodium hydroxide, potassium hydroxide, calcium hydroxide, lithium hydroxide, sodium carbonate, potassium carbonate, calcium carbonate, and lithium carbonate. Of these, a carbonate and/or a hydrogencarbonate of an alkali metal or an alkaline earth metal is preferred. Particularly, a base catalyst containing an alkali metal carbonate as a primary component is preferably employed. Industrially, a sodium salt is generally employed.

Examples of the organic base which may be employed include aliphatic amine compounds (in particular, tertiary amines), such as trimethylamine, triethylamine, diethylmethylamine, dimethylethylamine, triisopropylamine, and tributylamine.

Similar to the case of formaldehyde, as used herein, "base catalyst (1)" refers to one supplied in step I, and "base catalyst (2)" refers to one supplied in step III. In some cases, a base catalyst (2) is not supplied in step III, since the distillation residue obtained in step II contains a base catalyst (1).

The aforementioned base catalysts (inorganic bases and organic bases) may be employed singly or in combination of a plurality of species. For example, the base catalyst (1) may be triethylamine, and the base catalyst (2) may be sodium hydroxide. Alternatively, a plurality of inorganic bases or organic bases may be sequentially employed.

When a base catalyst containing an alkali metal carbonate as a primary component is employed, the carbonate is consumed in reaction, and a hydrogencarbonate generated by the reaction is converted through, for example, heating into the carbonate, which is consumed in the reaction. The base catalyst containing a carbonate as a primary component may be a carbonate which is generally commercially available as an industrial chemical, or may be a mixture of such a carbonate and a hydrogencarbonate. Alternatively, the base catalyst may be a carbonate produced from a hydrogencarbonate generated through oxidation or hydrolysis of a formate, or may be a mixture of such a carbonate and a hydrogencarbonate.

<Step I>

In step I, there is obtained a reaction mixture predominantly containing ECR and trimethylolpropane (TMP) produced through aldol condensation reaction and crossed Cannizzaro reaction between NBD and formaldehyde in the presence of a base catalyst (1).

In step I, reaction is carried out through, for example, a process in which NBD and a base catalyst (1) are added dropwise in parallel to an aqueous formaldehyde (1) solution; or a process in which the aqueous formaldehyde (1) solution is mixed with the base catalyst (1), and then NBD is added dropwise to the resultant mixture at a constant rate.

When NBD and the base catalyst (1) are added dropwise in parallel, preferably, each of them is added dropwise over 1 to 600 minutes, more preferably 10 to 360 minutes. When NBD is added dropwise to the mixture of the formaldehyde (1) and the base catalyst (1), the dropwise addition time is similar to that described above. From the viewpoint of improvement of production efficiency, the dropwise addition time is regulated to 600 minutes or shorter.

The amount of formaldehyde (1) employed in step I is 2.0 to 3.5 mol, preferably 2.0 to 3.0 mol, on the basis of 1 mol of NBD. When the amount of formaldehyde (1) is less than 2.0 mol, substantially no reaction of interest occurs, and a side reaction between NBD (raw material) molecules or by-production of bis-TMP is likely to occur, whereas when the amount of formaldehyde (1) exceeds 3.5 mol, the amount of ECR recovered through distillation is reduced, and the amount of di-TMP produced is reduced.

The amount of the base catalyst (1) employed in step I is 0.5 to 1.5 equivalents on the basis of 1.0 mol of NBD. When the amount of the base catalyst (1) is less than 0.5 equivalents, substantially no reaction for production of di-TMP (i.e., a product of interest) occurs, and, for example, a side reaction between NBD (raw material) molecules is likely to occur.

The amount of the base catalyst (1) employed varies depending on the type of the base, or reaction conditions (e.g., temperature and time). When a strong base (e.g., sodium hydroxide) is employed, the amount of the base is preferably in the vicinity of 0.5 equivalents (i.e., the lower limit of the aforementioned range), since the base participates in reaction immediately after addition to the reaction system. Employment of a large amount of such a strong base is not preferred, from the viewpoint of occurrence of side reactions. In contrast, when a weak base (e.g., sodium carbonate) is employed, the amount of the base is preferably in the vicinity of 1.5 equivalents (i.e., the upper limit of the aforementioned range), since the base exhibits low reactivity.

In step I, the reaction temperature is preferably 45 to 120° C., more preferably 60 to 110° C. After addition of NBD and the base catalyst (1) to the aqueous formaldehyde (1) solution, the resultant mixture may be heated at 45 to 120° C. for about 1 to about 300 minutes, to thereby allow reaction to proceed further. In such a case, the mixture may be pressurized with an inert gas (e.g., nitrogen gas) so that the reaction temperature in the reaction system is maintained at a certain level.

<Step II>

In step II, the reaction mixture obtained through step I is subjected to distillation, to thereby recover 2-ethyl-2-propenal (ECR). Separation/recovery of ECR produced in the reaction system in step I may be carried out in parallel with the reaction of step I (i.e., during the reaction), or after completion of the reaction.

Separation/recovery of ECR can be readily carried out through distillation at reduced pressure or ambient pressure, or under pressurized conditions. Preferably, ECR is entirely recovered. However, ECR may partially remain in the reaction system.

In step II, the distillation temperature is 45° C. to 120° C. When distillation is carried out at atmospheric pressure, the distillation temperature is preferably 90 to 110° C. The amount of ECR recovered through distillation is preferably 0.05 to 0.5 mol, more preferably 0.06 to 0.45 mol, much more preferably 0.1 to 0.35 mol, on the basis of 1.0 mol of NBD (i.e., a raw material). When ECR recovered in an amount falling within the above range is subjected to reaction in the subsequent step III, the amount of di-TMP produced is increased; i.e., di-TMP can be effectively produced.

Since ECR is co-boiled with water upon recovery of ECR through distillation, the resultant distillate contains water. Therefore, immediately after the distillate has been allowed to stand still, the distillate is separated into two layers; i.e., an oil layer (ECR-containing layer) and an aqueous layer. The amount of water co-distilled with ECR is preferably 0.01 to 20 times, more preferably 0.1 to 2.0 times the mass of ECR distilled.

When an aqueous formaldehyde solution for general industrial use is employed, since the aqueous formaldehyde solution contains methanol, methanol is co-distilled with ECR. When the amount of water co-distilled with ECR is regulated to be 0.01 times or more the mass of ECR distilled, since the distilled methanol dissolves in the aqueous layer, the methanol does not remain in the oil layer, and generation of by-products through reaction between methanol and ECR is prevented. Needless to say, when, for example, methanol-free formaldehyde or paraformaldehyde is employed as a raw material, generation of such a by-product can be avoided. However, from the industrial viewpoints (e.g., recovery efficiency), ECR is preferably recovered together with water for recovery of a sufficient amount of ECR. For prevention of long-term distillation in step II, the amount of water co-distilled with ECR is regulated to be 20 times or less the mass of ECR distilled.

The distillate obtained through step II contains ECR, water, and organic components (e.g., methanol). The distillate may be employed as is in step III, or may optionally be purified through, for example, distillation, and then employed for reaction with formaldehyde in step III.

When the distillate is separated into two layers (oil layer and aqueous layer), the distillate may be added as is to the distillation residue, or may be added thereto after, for example, mixing with stirring. Alternatively, the two layers may be separated from each other, and then the individual layers may be separately added to the distillation residue. Alternatively, one of the oil layer and the aqueous layer may be added to the distillation residue before addition of the other layer thereto.

The distillation residue contains, for example, TMP produced through step I, high-boiling-point substances, unreacted formaldehyde, water derived from an aqueous formaldehyde solution (i.e., a raw material), and water by-produced through crossed Cannizzaro reaction. The residue contains a large amount of TMP (i.e., one of products of interest), and also contains some amount of intermediates produced through incompletely proceeded reaction of interest. In order to convert the intermediates into TMP, preferably, after recovery of ECR through distillation, the distillation residue is heated at 45 to 120° C. for about 1 to about 300 minutes for completion of reaction.

<Step III>

In step III, ECR recovered through step II and formaldehyde (2), and optionally a base catalyst (2) are added to the TMP-containing distillation residue obtained through recovery of ECR in step II, to thereby allow reaction for production of di-TMP to proceed.

In step III, ECR is subjected to reaction with the distillation residue. As shown in the following reaction scheme, di-TMP is produced from TMP, ECR, and formaldehyde. This reaction produces formic acid (HCOOH), which reacts with the base catalyst to form a formate.

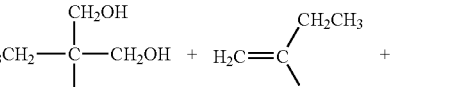

[F3]

The amount of formaldehyde (2) supplied in step III is determined by subtracting the amount of formaldehyde added in step I from the required total amount of formaldehyde that has been predetermined on the basis of the amount of NBD employed as a raw material.

Specifically, the amount of formaldehyde (2) supplied is determined so that the total amount of formaldehyde (1) and formaldehyde (2) is 3.0 to 4.5 mol, preferably 3.0 to 4.0 mol, more preferably 3.1 to 3.5 mol, on the basis of 1.0 mol of n-butyraldehyde serving as a raw material. When the total amount of formaldehyde (1) and formaldehyde (2) is less than 3.0, the amount of di-TMP produced is reduced, and becomes equal to or smaller than the theoretical amount of di-TMP obtained through the aforementioned reaction for di-TMP production, and thus the amount of by-products increases. In contrast, when the total amount of formaldehyde (1) and formaldehyde (2) exceeds 4.5 mol, the yield of di-TMP on the basis of TMP is reduced, and the amount of bis-TMP (i.e., a by-product) produced increases.

Similar to the case of formaldehyde (2), the amount of the base catalyst (2) employed in step III is determined by subtracting the amount of the base catalyst (1) employed in step I from the total amount of the base catalyst (1) and base catalyst (2). The total amount is adjusted to 1.0 to 2.5 equivalents (preferably 1.0 to 1.5 equivalents) on the basis of 1.0 mol of n-butyraldehyde serving as a raw material.

For example, when the base catalyst (1) and the base catalyst (2) are a divalent base (2.0 equivalents) such as sodium carbonate or calcium hydroxide, the total amount of the base catalyst (1) and the base catalyst (2) is regulated to be 1.0 to 2.5 equivalents (0.5 to 1.25 mol) on the basis of 1.0 mol of NBD. When the total amount is less than 1.0 equivalent, a large amount of unreacted raw material remains in the reaction system, and side reactions are likely to occur from the unreacted raw material, whereas when the total amount exceeds 2.5 equivalents, a large amount of an acid is required for neutralization of excess base.

When ECR recovered through distillation and formaldehyde (2), and optionally the base catalyst (2) are added dropwise to the distillation residue obtained through recovery of ECR in step II, preferably, each of these substances—which are added dropwise in, for example, a sequential or parallel manner—is continuously added dropwise over 1 to 300 minutes. When these substances are added dropwise in parallel, dropwise addition of any of them may be terminated before termination of dropwise addition of the other substance(s).

In step III, the reaction temperature, which may vary with the type of the base employed, is preferably 45 to 120° C., more preferably 60 to 120° C. Particularly when the base catalyst employed is a carbonate, the reaction temperature is preferably 60 to 120° C., more preferably 80 to 120° C., since the temperature must be maintained at such a level that conversion of a hydrogencarbonate generated through reaction to the carbonate proceeds sufficiently. Similar to the case of step I, in step III, the reaction mixture may be pressurized with an inert gas (e.g., nitrogen gas) so that the reaction temperature in the reaction system is maintained at a certain level.

When ECR (i.e., a raw material of di-TMP) is not completely consumed at the time of termination of addition of ECR recovered through distillation and formaldehyde (2), and optionally the base catalyst (2) to the distillation residue obtained through recovery of ECR in step II, preferably, heating is further continued for completion of reaction. In this case, the reaction temperature, which may vary with the type of the base employed, is preferably 45 to 120° C., more preferably 60 to 120° C. Particularly when the base catalyst (2) employed is a carbonate, the reaction temperature is preferably 60 to 120° C., more preferably 80 to 120° C., since the temperature must be maintained at such a level that conversion of a hydrogencarbonate generated through reaction to the carbonate proceeds sufficiently. In this case, the reaction mixture may also be pressurized with an inert gas (e.g., nitrogen gas) so that the reaction temperature in the reaction system is maintained at a certain level. The time required for completion of reaction through this heating is preferably 1 to 180 minutes, more preferably 30 to 120 minutes. The heating time is regulated to be 180 minutes or shorter so as to prevent coloring of the reaction mixture.

In the present invention, the reactions of step I and step III may be carried out in different reactors under the same or different reaction conditions. Alternatively, the reactions may be sequentially carried out in the same reactor. For example, when the reactions are carried out in different reactors, triethylamine is employed as the base catalyst (1) in the reaction of step I, and subsequently, sodium hydroxide is employed as the base catalyst (2) in the reaction of step III.

<Isolation of di-TMP>

No particular limitation is imposed on the process for isolating di-TMP (i.e., a product of interest) from the reaction mixture obtained through step III and purifying the thus-isolated di-TMP, and isolation/purification may be carried out through a generally used process for TMP purification as disclosed in, for example, Patent Documents 2 to 5 described in "Background Art." In an example process, the reaction mixture is neutralized and then formaldehyde (i.e., a raw material) is recovered through distillation; the distillation residue is subjected to extraction; and subsequently di-TMP is recovered and purified through distillation or crystallization.

All the reactions and operations in the present invention (including steps I to III and di-TMP isolation) may be carried out in apparatuses provided exclusively for the respective reactions and operations. Alternatively, these reactions and operations may be carried out in one or a plurality of apparatuses which can be adapted therefor.

EXAMPLES

The present invention will next be described in more detail by way of examples, which should not be construed as limiting the invention thereto.

In the below-described Examples, commercially available reagents, etc. were employed as raw materials; specifically, NBD: special grade reagent (product of Aldrich); aqueous formaldehyde solution: 40 mass % aqueous formaldehyde solution for industrial use (methanol content: 3 mass %, product of Mitsubishi Gas Chemical Company, Inc.); and sodium carbonate: special grade reagent (product of Wako Pure Chemical Industries, Ltd.).

Analysis was carried out through gas chromatography (GC), and samples and an internal standard material were diluted with acetone (solvent).

[Gas Chromatographic Analysis Conditions]

Apparatus: HP-5890 (product of Agilent Technologies Japan, Ltd.)

Column employed: DB-1 (product of Agilent Technologies Japan, Ltd.)

Analysis conditions: injection temperature: 250° C., detector temperature: 250° C.

Column temperature: 60° C. for 6 minutes→elevated to 250° C. at 7 degrees (° C.)/minute→250° C. for 20 minutes Detector: flame ionization detector (FID)

Example 1

Proportions by Mole of Raw Materials Employed; NBD:formaldehyde (1):formaldehyde (2)=1:2.8:0.6)

Step I: A 40 mass % aqueous formaldehyde (1) solution (208.7 g, 2.8 mol as reduced to formaldehyde, 82% of the total amount of formaldehyde employed) was added to a four-necked flask (1,000 mL) equipped with a reflux condenser, a thermometer, and two dropping funnels, followed by heating to 72° C. Subsequently, NBD (72 g, 1.0 mol) and 21 mass % aqueous sodium carbonate solution (263 g, 0.53 mol=1.06 equivalents) were entirely added through the dropping funnels to the flask over 25 minutes with gradually heating, and heating was further continued at 80° C. for two minutes, to thereby produce a reaction mixture.

Step II: The reaction mixture obtained in step I was heated to 100° C., and distillation was carried out for 30 minutes, to thereby recover ECR. The liquid recovered through distillation was found to contain an oil layer (22 mL, ECR: 0.16 mol) and an aqueous layer (9 mL). The amount of water co-distilled with ECR was found to be 0.5 times the mass of ECR distilled.

Step III: The ECR distillate obtained in step II and 18 mass % aqueous formaldehyde (2) solution (103 g, 0.62 mol, 18% of the total amount of formaldehyde employed) were added at 96° C. to the distillation residue obtained in step II over 48 minutes and 90 minutes, respectively. After completion of dropwise addition, heating was further continued at 100° C. for 60 minutes, to thereby allow reaction for production of di-TMP to proceed.

The resultant reaction mixture was subjected to GC analysis. As a result, the amounts of produced TMP, di-TMP, and bis-TMP were found to be 90.5 g, 18.8 g, and 2.8 g, respectively, and the yields of TMP, di-TMP, and bis-TMP on the basis of NBD (raw material) were found to be 67.5%, 15.0%, and 2.0%, respectively.

Example 2

Proportions by Mole of Raw Materials Employed; NBD:formaldehyde (1):formaldehyde (2)=1:2.6:0.6)

Step I: A 40 mass % aqueous formaldehyde (1) solution (194 g, 2.6 mol as reduced to formaldehyde, 81% of the total amount of formaldehyde employed) was added to a four-necked flask (1,000 mL) equipped with a reflux condenser, a thermometer, and two dropping funnels, followed by heating to 74° C. Subsequently, NBD (72 g, 1.0 mol) and 21 mass % aqueous sodium carbonate solution (263 g, 0.53 mol=1.06 equivalents) were entirely added through the two dropping funnels to the flask over 25 minutes with gradually heating, and heating was further continued at 80° C. for three minutes, to thereby produce a reaction mixture.

Step II: The reaction mixture obtained in step I was heated to 100° C., and distillation was carried out for 30 minutes, to thereby recover ECR. The distillate recovered through distillation was found to contain an oil layer (26 mL, ECR: 0.19 mol) and an aqueous layer (5 mL). The amount of water co-distilled with ECR was found to be 0.2 times the mass of ECR distilled.

Step III: The ECR distillate obtained in step II and 18 mass % aqueous formaldehyde (2) solution (103 g, 0.62 mol as reduced to formaldehyde, 19% of the total amount of formaldehyde employed) were added through the two dropping funnels to the distillation residue obtained in step II over minutes and 80 minutes, respectively, while the temperature of the resultant reaction mixture was maintained at 92° C. After completion of dropwise addition, heating was further continued at 100° C. for 80 minutes, to thereby allow reaction for production of di-TMP to proceed.

The resultant reaction mixture was subjected to GC analysis. As a result, the amounts of produced TMP, di-TMP, and bis-TMP were found to be 86 g, 22 g, and 2 g, respectively, and the yields of TMP, di-TMP, and bis-TMP on the basis of NBD (raw material) were found to be 64.3%, 17.5%, and 1.4%, respectively.

Example 3

Proportions by Mole of Raw Materials Employed; NBD:formaldehyde (1):formaldehyde (2)=1:2.4:0.8)

Step I: A 40 mass % aqueous formaldehyde (1) solution (179 g, 2.4 mol as reduced to formaldehyde, 75% of the total amount of formaldehyde employed) was added to a four-necked flask (1,000 mL) equipped with a reflux condenser, a thermometer, and two dropping funnels, followed by heating to 73° C. Subsequently, NBD (72 g, 1.0 mol) and 21 mass % aqueous sodium carbonate solution (263 g, 0.53 mol=1.06 equivalents) were entirely added through the dropping funnels to the flask over 25 minutes with gradually heating, and heating was further continued at 84° C. for three minutes, to thereby allow reaction for production of di-TMP to proceed.

Step II: The reaction mixture obtained in step I was heated to 100° C., and distillation was carried out for 30 minutes, to thereby recover ECR. The liquid recovered through distillation was found to contain an oil layer (32 mL, ECR: 0.24 mol) and an aqueous layer (6 mL). The amount of water co-distilled with ECR was found to be 0.2 times the mass of ECR distilled.

Step III: The ECR distillate obtained in step II and 21 mass % aqueous formaldehyde (2) solution (118 g, 0.82 mol, 25% of the total amount of formaldehyde employed) were added at 94° C. to the distillation residue obtained in step II over 60 minutes and 110 minutes, respectively. After completion of dropwise addition, heating was further continued at 99° C. for 60 minutes.

The resultant reaction mixture was subjected to GC analysis. As a result, the amounts of produced TMP, di-TMP, and bis-TMP were found to be 79.0 g, 23.3 g, and 2.2 g, respectively, and the yields of TMP, di-TMP, and bis-TMP on the basis of NBD (raw material) were found to be 58.9%, 18.6%, and 1.6%, respectively.

Example 4

Proportions by Mole of Raw Materials Employed; NBD:formaldehyde (1):formaldehyde (2)=1:2.6:0.6)

Step I: A 40 mass % aqueous formaldehyde (1) solution (194 g, 2.6 mol as reduced to formaldehyde, 81% of the total amount of formaldehyde employed) was added to a four-necked flask (1,000 mL) equipped with a reflux condenser, a thermometer, and two dropping funnels, followed by heating to 72° C. Subsequently, NBD (72 g, 1.0 mol) and 21 mass % aqueous sodium carbonate solution (251 g, 0.50 mol=1.0 equivalent) were entirely added through the dropping funnels to the flask over 25 minutes with gradually heating, and heating was further continued at 85° C. for three minutes.

Step II: The reaction mixture obtained in step I was heated to 100° C., and distillation was carried out for 30 minutes, to thereby recover ECR. The recovered liquid was found to contain an oil layer (23 mL, ECR: 0.17 mol) and an aqueous layer (7 mL). The amount of water co-distilled with ECR was found to be 0.38 times the mass of ECR distilled.

Step III: The ECR distillate obtained in step II and a 24 mass % aqueous formaldehyde (2) solution (76 g, 0.62 mol, 19% of the total amount of formaldehyde employed) were added at 90° C. to the distillation residue obtained in step II over 88 minutes and 90 minutes, respectively. After completion of dropwise addition, heating was further continued at 98° C. for 90 minutes. The resultant reaction mixture was subjected to GC analysis. As a result, the amounts of produced TMP, di-TMP, and bis-TMP were found to be 80.2 g, 17.6 g, and 2.3 g, respectively, and the yields of TMP, di-TMP, and bis-TMP on the basis of NBD (raw material) were found to be 59.8%, 14.1%, and 1.6%, respectively.

Example 5

Proportions by Mole of Raw Materials Employed; NBD:formaldehyde (1):formaldehyde (2)=1:3.5:0.5)

Step I: A 40 mass % aqueous formaldehyde (1) solution (262.8 g, 3.5 mol as reduced to formaldehyde, 87.5% of the total amount of formaldehyde employed) was added to a four-necked flask (1,000 mL) equipped with a reflux condenser, a thermometer, and two dropping funnels, followed by heating to 74° C. Subsequently, NBD (72 g, 1.0 mol) and 21 mass % aqueous sodium carbonate solution (263 g, 0.53 mol=1.06 equivalents) were entirely added through the dropping funnels to the flask over 25 minutes with gradually heating, and heating was further continued at 85° C. for three minutes.

Step II: The reaction mixture obtained in step I was heated to 100° C., and distillation was carried out for 30 minutes, to thereby recover ECR. The recovered liquid was found to contain an oil layer (14 mL, ECR: 0.12 mol) and an aqueous layer (5 mL). The amount of water co-distilled with ECR was found to be 0.50 times the mass of ECR distilled.

Step III: The ECR distillate obtained in step II and a 39 mass % aqueous formaldehyde (2) solution (76 g, 0.5 mol, 12.5% of the total amount of formaldehyde employed) were added at 100° C. to the distillation residue obtained in step II over 33 minutes and 90 minutes, respectively. After completion of dropwise addition, heating was further continued at 100° C. for 45 minutes. The resultant reaction mixture was subjected to GC analysis. As a result, the amounts of produced TMP, di-TMP, and bis-TMP were found to be 99.3 g, 10.0 g, and 4.7 g, respectively, and the yields of TMP, di-TMP, and bis-TMP on the basis of NBD (raw material) were found to be 74.2%, 8.0%, and 3.4%, respectively.

Example 6

Proportions by Mole of Raw Materials Employed; NBD:formaldehyde (1):formaldehyde (2)=1:3.0:1.0)

Step I: A 40 mass % aqueous formaldehyde (1) solution (225 g, 3.0 mol as reduced to formaldehyde, 75% of the total amount of formaldehyde employed) was added to a four-necked flask (1,000 mL) equipped with a reflux condenser, a thermometer, and two dropping funnels, followed by heating to 73° C. Subsequently, NBD (72 g, 1.0 mol) and 21 mass % aqueous sodium carbonate solution (263 g, 0.53 mol=1.06 equivalents) were entirely added through the dropping funnels to the flask over 25 minutes with gradually heating, and heating was further continued at 85° C. for three minutes.

Step II: The reaction mixture obtained in step I was heated to 98° C., and distillation was carried out for 20 minutes, to thereby recover ECR. The recovered liquid was found to contain an oil layer (18 mL, ECR: 0.16 mol) and an aqueous layer (8 mL). The amount of water co-distilled with ECR was found to be 0.53 times the mass of ECR distilled.

Step III: The ECR distillate obtained in step II and a 40 mass % aqueous formaldehyde (2) solution (74.8 g, 1.0 mol, 25% of the total amount of formaldehyde employed) were added at 98° C. to the distillation residue obtained in step II over 45 minutes and 90 minutes, respectively. After completion of dropwise addition, heating was further continued at 101° C. for 60 minutes. The resultant reaction mixture was subjected to GC analysis. As a result, the amounts of produced TMP, di-TMP, and bis-TMP were found to be 94.6 g, 15.0 g, and 4.7 g, respectively, and the yields of TMP, di-TMP, and bis-TMP on the basis of NBD (raw material) were found to be 70.6%, 12.0%, and 3.3%, respectively.

Example 7

Proportions by Mole of Raw Materials Employed; NBD:formaldehyde (1):formaldehyde (2)=1:2.6:1.4)

Step I: A 40 mass % aqueous formaldehyde (1) solution (195 g, 2.6 mol as reduced to formaldehyde, 65% of the total amount of formaldehyde employed) was added to a four-necked flask (1,000 mL) equipped with a reflux condenser, a thermometer, and two dropping funnels, followed by heating to 74° C. Subsequently, NBD (72 g, 1.0 mol) and 21 mass % aqueous sodium carbonate solution (264.5 g, 0.53 mol=1.06 equivalents) were entirely added through the dropping funnels to the flask over 25 minutes with gradually heating, and heating was further continued at 79° C. for three minutes.

Step II: The reaction mixture obtained in step I was heated to 98° C., and distillation was carried out for 26 minutes, to thereby recover ECR. The recovered liquid was found to contain an oil layer (25 mL, ECR: 0.23 mol) and an aqueous layer (5 mL). The amount of water co-distilled with ECR was found to be 0.53 times the mass of ECR distilled.

Step III: The ECR distillate obtained in step II and a 40 mass % aqueous formaldehyde (2) solution (100.5 g, 1.4 mol, 35% of the total amount of formaldehyde employed) were added at 92° C. to the distillation residue obtained in step II over 55 minutes and 83 minutes, respectively. After completion of dropwise addition, heating was further continued at 100° C. for 90 minutes. The resultant reaction mixture was subjected to GC analysis. As a result, the amounts of produced TMP, di-TMP, and bis-TMP were found to be 85.9 g, 18.8 g, and 4.6 g, respectively, and the yields of TMP, di-TMP, and bis-TMP on the basis of NBD (raw material) were found to be 64.1%, 15.0%, and 3.3%, respectively.

Example 8

Proportions by Mole of Raw Materials Employed; NBD:formaldehyde (1):formaldehyde (2)=1:2.4:0.8)

Step I: A 40 mass % aqueous formaldehyde (1) solution (179 g, 2.4 mol as reduced to formaldehyde, 75% of the total amount of formaldehyde employed) was added to a four-necked flask (1,000 mL) equipped with a reflux condenser, a thermometer, and two dropping funnels, followed by heating to 73° C. Subsequently, NBD (72 g, 1.0 mol) and 21 mass % aqueous sodium carbonate solution (184 g, 0.37 mol=0.74 equivalents) were entirely added through the dropping funnels to the flask over 25 minutes with gradually heating, and heating was further continued at 84° C. for three minutes.

Step II: After completion of heating, ECR was recovered through distillation at 99° C. for 30 minutes. The liquid recovered through distillation was found to contain an oil layer (33 mL, ECR: 0.25 mol) and an aqueous layer (6 mL). The amount of water co-distilled with ECR was found to be 0.2 times the mass of ECR distilled.

Step III: The thus-obtained distillate, 21 mass % aqueous formaldehyde (2) solution (118 g, 0.82 mol, 25% of the total amount of formaldehyde employed), and a 20% aqueous sodium hydroxide solution (64.0 g, 0.32 mol=0.32 equivalents) were added at 94° C. to the distillation residue over 60 minutes, 110 minutes, and 90 minutes, respectively. After completion of dropwise addition, heating was further continued at 99° C. for 60 minutes.

The resultant reaction mixture was subjected to GC analysis. As a result, the amounts of produced TMP, di-TMP, and bis-TMP were found to be 80.9 g, 45.0 g, and 2.2 g, respectively, and the yields of TMP, di-TMP, and bis-TMP on the basis of NBD (raw material) were found to be 60.4%, 18.0%, and 1.6%, respectively.

Comparative Example 1

Proportions by Mole of Raw Materials Employed; NBD:formaldehyde (1):formaldehyde (2)=1:4.0:0)

Step I: A 40 mass % aqueous formaldehyde (1) solution (300.3 g, 4.0 mol as reduced to formaldehyde, 100% of the total amount of formaldehyde employed) was added to a four-necked flask (1,000 mL) equipped with a reflux condenser, a thermometer, and two dropping funnels, followed by heating to 73° C. Subsequently, NBD (72 g, 1.0 mol) and 21 mass % aqueous sodium carbonate solution (263 g, 0.53 mol=1.06 equivalents) were entirely added through the dropping funnels to the flask over 25 minutes with gradually heating, and heating was further continued at 85° C. for three minutes.

Step II: The reaction mixture obtained in step I was heated to 98° C., and distillation was carried out for 20 minutes, to thereby recover ECR. The recovered liquid was found to contain an oil layer (11 mL, ECR: 0.11 mol) and an aqueous layer (3 mL). The amount of water co-distilled with ECR was found to be 0.34 times the mass of ECR distilled.

Step III: The ECR distillate obtained in step II was added at 92° C. to the distillation residue obtained in step II over 20 minutes. After completion of dropwise addition, heating was further continued at 100° C. for 60 minutes. The resultant reaction mixture was subjected to GC analysis. As a result, the amounts of produced TMP, di-TMP, and bis-TMP were found to be 102.5 g, 6.9 g, and 5.3 g, respectively, and the yields of TMP, di-TMP, and bis-TMP on the basis of NBD (raw material) were found to be 76.5%, 4.4%, and 3.8%, respectively.

Comparative Example 2

Conventional Production Method, No Recovery of ECR, Addition of Formaldehyde and Base at One Time A 32 mass % aqueous formaldehyde solution (297 g, 3.2 mol as reduced to formaldehyde) was entirely added to a four-necked flask (1,000 mL) equipped with a reflux condenser, a thermometer, and two dropping funnels, followed by heating to 73° C. Subsequently, NBD (72 g, 1.0 mol) and 21 mass % aqueous sodium carbonate solution (264 g, 0.53 mol=1.06 equivalents) were entirely added through the dropping funnels to the flask over 184 minutes and 25 minutes, respectively, with gradually heating. After completion of addition, heating was continued at 89° C. for 180 minutes. The resultant reaction mixture was subjected to GC analysis. As a result, the amounts of produced TMP, di-TMP, and bis-TMP were found to be 90.8 g, 3.9 g, and 2.2 g, respectively, and the yields of TMP, di-TMP, and bis-TMP on the basis of NBD (raw material) were found to be 67.7%, 3.1%, and 1.6%, respectively.

Comparative Example 3

Proportions by Mole of Raw Materials Employed; NBD:formaldehyde (1):formaldehyde (2)=1:2.0:0.2

Step I: A 31 mass % aqueous formaldehyde (1) solution (195 g, 2.0 mol as reduced to formaldehyde, 91% of the total amount of formaldehyde employed) was added to a four-necked flask (1,000 mL) equipped with a reflux condenser, a thermometer, and two dropping funnels, followed by heating to 74° C. Subsequently, NBD (72 g, 1.0 mol) and 21 mass % aqueous sodium carbonate solution (263 g, 0.53 mol=1.06 equivalents) were entirely added through the dropping funnels to the flask over 25 minutes with gradually heating, and heating was further continued at 82° C. for three minutes.

Step II: The reaction mixture obtained in step I was heated to 98° C., and distillation was carried out for 35 minutes, to thereby recover ECR. The recovered liquid was found to contain an oil layer (42 mL, ECR: 0.41 mol) and an aqueous layer (6 mL). The amount of water co-distilled with ECR was found to be 0.17 times the mass of ECR distilled.

Step III: The ECR distillate obtained in step II and an 8 mass % aqueous formaldehyde (2) solution (76 g, 0.2 mol, 9% of the total amount of formaldehyde employed) were added at 82° C. to the distillation residue obtained in step II over 47 minutes and 102 minutes, respectively. After completion of dropwise addition, heating was further continued at 84° C. for 62 minutes (reflux state). The resultant reaction mixture was subjected to GC analysis. As a result, the amounts of produced TMP, di-TMP, and bis-TMP were found to be 59.8 g, 5.5 g, and 0.34 g, respectively, and the yields of TMP, di-TMP, and bis-TMP on the basis of NBD (raw material) were found to be 44.6%, 4.4%, and 0.2%, respectively.

Comparative Example 4

Proportions by Mole of Raw Materials Employed; NBD:formaldehyde (1):formaldehyde (2)=1:2.6:0.6

Step I: A 40 mass % aqueous formaldehyde (1) solution (194 g, 2.6 mol as reduced to formaldehyde, 81% of the total amount of formaldehyde employed) was added to a four-necked flask (1,000 mL) equipped with a reflux condenser, a thermometer, and two dropping funnels, followed by heating to 72° C. Subsequently, NBD (72 g, 1.0 mol) and 21 mass % aqueous sodium carbonate solution (251 g, 0.50 mol=1.0 equivalent) were entirely added through the dropping funnels to the flask over 25 minutes with gradually heating, and heating was further continued at 85° C. for three minutes.

Step II: 2-Ethyl-2-propenal was not recovered through distillation, and the reaction mixture was subjected to the subsequent step.

Step III: A 24 mass % aqueous formaldehyde (2) solution (76 g, 0.62 mol, 19% of the total amount of formaldehyde employed) was added at 86° C. to the reaction mixture over 90 minutes. After completion of dropwise addition, heating was further continued at 88° C. for 90 minutes under reflux. The resultant reaction mixture was subjected to GC analysis. As a result, the amounts of produced TMP, di-TMP, and bis-TMP were found to be 89.4 g, 9.8 g, and 5.6 g, respectively, and the yields of TMP, di-TMP, and bis-TMP on the basis of NBD (raw material) were found to be 66.7%, 3.9%, and 2.0%, respectively.

Comparative Example 5

Proportions by Mole of Raw Materials Employed; NBD:formaldehyde (1):formaldehyde (2)=1:2.6:0.6

Step I: A 40 mass % aqueous formaldehyde (1) solution (194 g, 2.6 mol as reduced to formaldehyde, 81% of the total amount of formaldehyde employed) was added to a four-necked flask (1,000 mL) equipped with a reflux condenser, a thermometer, and two dropping funnels, followed by heating to 40° C. Subsequently, NBD (72 g, 1.0 mol) and 21 mass % aqueous sodium hydroxide solution (142.8 g, 0.75 mol=0.75 equivalents) were entirely added through the dropping funnels to the flask over 25 minutes with gradually heating, and heating was further continued at 40° C. for three minutes.

Step II: After completion of heating, ECR was recovered through distillation at 98° C. for 20 minutes. The recovered liquid was found to contain an oil layer (1.2 mL, ECR: 0.01 mol) and an aqueous layer (10 mL). The amount of water co-distilled with ECR was found to be 10 times the mass of ECR distilled.

Step III: A 24 mass % aqueous formaldehyde (2) solution (76 g, 0.62 mol, 19% of the total amount of formaldehyde employed) and 21 mass % aqueous sodium hydroxide solution (47.6 g, 0.25 mol=0.25 equivalents) were added at 50° C. to the distillation residue over 90 minutes. After completion of dropwise addition, heating was further continued at 80° C. for 90 minutes. The resultant reaction mixture was subjected to GC analysis. As a result, the amounts of produced TMP, di-TMP, and bis-TMP were found to be 111 g, 13.1 g, and 5.9 g, respectively, and the yields of TMP, di-TMP, and bis-TMP on the basis of NBD (raw material) were found to be 82.5%, 5.3%, and 2.1%, respectively.

Tables 1 and 2 show main operation conditions and yields in the aforementioned Examples and Comparative Examples. Comparison between the data in Tables 1 and 2 shows that, in the Examples, the yield of di-TMP is considerably increased; i.e., di-TMP is effectively produced. As is clear from these data, particularly when the amounts of formaldehyde (1) and formaldehyde (2) supplied are regulated with respect to 1.0 mol of NBD (raw material), the amount of bis-TMP by-produced can be considerably reduced, and di-TMP (i.e., a product of interest) can be produced more effectively and advantageously.

TABLE 1

|  | Ex. 1 | Ex. 2 | Ex. 3 | Ex. 4 | Ex. 5 | Ex. 6 | Ex. 7 | Ex. 8 |
|---|---|---|---|---|---|---|---|---|
| Amount with respect to 1.0 mol of NBD | | | | | | | | |
| Step I: Formaldehyde (1): mol | 2.8 | 2.6 | 2.4 | 2.6 | 3.5 | 3.0 | 2.6 | 2.4 |
| Base catalyst (1): equivalent | 1.06 | 1.06 | 1.06 | 1.00 | 1.06 | 1.06 | 1.06 | 0.74 |
| Step II: ECR: mol | 0.16 | 0.19 | 0.24 | 0.17 | 0.12 | 0.16 | 0.23 | 0.25 |
| Step III: Formaldehyde (2): mol | 0.62 | 0.62 | 0.82 | 0.62 | 0.5 | 1.0 | 1.4 | 0.82 |
| Base catalyst (2): equivalent | | | | | | | | 0.32 |
| Formaldehydes (1) + (2): mol | 3.42 | 3.22 | 3.22 | 3.22 | 4.00 | 4.00 | 4.00 | 3.22 |
| Base catalysts (1) + (2): equivalent | 1.06 | 1.06 | 1.06 | 1.00 | 1.06 | 1.06 | 1.06 | 1.06 |
| Temperature (° C.) | | | | | | | | |
| Step I (dropwise addition/heating) | 72/80 | 74/80 | 73/84 | 72/85 | 74/85 | 73/85 | 74/79 | 73/84 |
| Step II (distillation) | 100 | 100 | 99 | 98 | 98 | 98 | 98 | 99 |
| Step III (dropwise addition/heating) | 96/100 | 92/100 | 94/99 | 90/98 | 100/100 | 98/101 | 92/100 | 94/99 |
| Amount of water co-distilled with ECR (fold by mass with respect to ECR) | 0.5 | 0.2 | 0.2 | 0.38 | 0.5 | 0.53 | 0.26 | 0.2 |
| Yield (mol %, on the basis of NBD) | | | | | | | | |
| TMP | 67.5 | 64.3 | 58.9 | 59.8 | 74.2 | 70.6 | 64.1 | 60.4 |
| di-TMP | 15.0 | 17.5 | 18.6 | 14.1 | 8.0 | 12.0 | 15.0 | 18.0 |
| bis-TMP | 2.0 | 0.8 | 1.6 | 1.6 | 3.4 | 3.3 | 3.3 | 1.6 |

TABLE 2

|  | Comp. Ex. 1 | Comp. Ex. 2 | Comp. Ex. 3 | Comp. Ex. 4 | Comp. Ex. 5 |
|---|---|---|---|---|---|
| Amount with respect to 1.0 mol of NBD | | | | | |
| Step I: Formaldehyde (1): mol | 4.0 | 3.2 | 2.0 | 2.6 | 2.6 |
| Base catalyst (1): equivalent | 1.06 | 1.06 | 1.06 | 1.00 | 0.75 |
| Step II: ECR: mol | 0.11 | | 0.41 | | 0.01 |
| Step III: Formaldehyde (2): mol | | | 0.2 | 0.62 | 0.62 |
| Base catalyst (2): equivalent | | | | | 0.25 |
| Formaldehydes (1) + (2): mol | 4.0 | 3.2 | 2.2 | 3.22 | 3.22 |
| Base catalysts (1) + (2): equivalent | 1.06 | 1.06 | 1.06 | 1.00 | 1.00 |
| Temperature (° C.) | | | | | |
| Step I (dropwise addition/heating) | 73/85 | 73/85 | 74/82 | 72/85 | 40/40 |
| Step II (distillation) | 98 | | 98 | | 98 |
| Step III (dropwise addition/heating) | 92/100 | | 82/84 | 86/90 | 50/80 |
| Amount of water co-distilled with ECR (fold by mass with respect to ECR) | 0.34 | | 0.17 | | 10 |
| Yield (mol %, on the basis of NBD) | | | | | |
| TMP | 76.5 | 67.7 | 44.6 | 66.7 | 82.5 |
| di-TMP | 4.4 | 3.1 | 4.4 | 3.9 | 5.3 |
| bis-TMP | 3.8 | 1.6 | 0.2 | 2.0 | 2.1 |

INDUSTRIAL APPLICABILITY

According to the present invention, in a method for reacting n-butyraldehyde with formaldehyde in the presence of a base catalyst, ECR produced is separated through distillation, and the thus-separated ECR is reacted with the TMP-containing distillation residue under specific conditions, whereby the yield of di-TMP is considerably increased. According to the present invention, the amount of bis-TMP by-produced can be considerably reduced with respect to the amount of di-TMP (i.e., a product of interest) produced; i.e., di-TMP can be effectively and industrially advantageously produced.

The thus-produced di-TMP is effectively employed as a raw material of, for example, polyacrylate, polyether polyol, polyurethane, alkyd resin, or a synthetic lubricant.

The invention claimed is:

1. A method for producing ditrimethylolpropane comprising reacting n-butyraldehyde with formaldehyde in the presence of a base catalyst to thereby produce trimethylolpropane and ditrimethylolpropane, wherein said method comprises:

(I) reacting n-butyraldehyde with formaldehyde (1) in the presence of a base catalyst (1), to thereby produce a reaction mixture containing trimethylolpropane, ditrimethylolpropane, and 2-ethyl-2-propenal;

(II) recovering 2-ethyl-2-propenal through distillation of the reaction mixture produced in I; and (III) directly adding, to a distillation residue obtained through recovery of 2-ethyl-2-propenal in II, the recovered 2-ethyl-2-propenal and formaldehyde (2), and optionally a base catalyst (2), to thereby allow the reaction for the production of ditrimethylolpropane to proceed, wherein, on the basis of 1.0 mol of n-butyraldehyde serving as a raw material, (a) the amount of formaldehyde (1) supplied is 2.0 to 3.5 mol;

(b) the total amount of formaldehyde (1) and formaldehyde (2) supplied is 3.0 to 4.5 mol;

(c) the amount of the base catalyst (1) supplied is 0.5 to 1.5 equivalents;

(d) the total amount of the base catalyst (1) and the base catalyst (2) supplied is 1.0 to 2.5 equivalents; and (e) the amount of 2-ethyl-2-propenal recovered in II is 0.05 to 0.5 mol.

2. The method for producing ditrimethylolpropane according to claim 1, wherein the reaction temperature in I is from 45 to 120° C.

3. The method for producing ditrimethylolpropane according to claim 1, wherein the distillation temperature in II is from 45° C. to 120° C.

4. The method for producing ditrimethylolpropane according to claim 1, wherein, in II, 2-ethyl-2-propenal is recovered in the form of a distillate mixture containing water in an amount of 0.01 to 20 times the mass of 2-ethyl-2-propenal distilled.

5. The method for producing ditrimethylolpropane according to claim 1, wherein, in III, the reaction is carried out at 45 to 120° C.

6. The method for producing ditrimethylolpropane according to claim 1, wherein the 2-ethyl-2-propenal is completely recovered through the distillation.

7. The method for producing ditrimethylolpropane according to claim 1, wherein the 2-ethyl-2-propenal is not completely recovered through the distillation.

8. The method for producing ditrimethylolpropane according to claim 1, wherein the amount of the 2-ethyl-2-propenal recovered is 0.06 to 0.45 mol based on 1.0 mol of n-butyraldehyde.

9. The method for producing ditrimethylolpropane according to claim 1, wherein the amount of the 2-ethyl-2-propenal recovered is 0.1 to 0.35 mol based on 1.0 mol of n-butyraldehyde.

10. The method for producing ditrimethylolpropane according to claim 1, wherein the recovered 2-ethyl-2-propenal is added to the distillation residue in (III) over 1 to 300 minutes.

11. The method for producing ditrimethylolpropane according to claim 1, wherein the reaction in (I) and (III) are conducted under different reaction conditions.

12. The method for producing ditrimethylolpropane according to claim 1, further comprising isolating the ditrimethylolpropane by distillation or crystallization.

* * * * *